US012735393B2

(12) United States Patent
Yoshida et al.

(10) Patent No.: US 12,735,393 B2
(45) Date of Patent: Sep. 15, 2026

(54) COMPOUND, CORROSION INHIBITOR, AND LUBRICANT COMPOSITION

(71) Applicant: IDEMITSU KOSAN CO., LTD., Chiyoda-ku (JP)

(72) Inventors: Yukio Yoshida, Ichihara (JP); Yusuke Nakanishi, Ichihara (JP); Hideaki Hattori, Edogawa-ku (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 585 days.

(21) Appl. No.: 18/258,045

(22) PCT Filed: Dec. 24, 2021

(86) PCT No.: PCT/JP2021/048244

§ 371 (c)(1),
(2) Date: Jun. 16, 2023

(87) PCT Pub. No.: WO2022/138931

PCT Pub. Date: Jun. 30, 2022

(65) Prior Publication Data

US 2024/0124407 A1 Apr. 18, 2024

(30) Foreign Application Priority Data

Dec. 25, 2020 (JP) ................................ 2020-218038

(51) Int. Cl.
*C07D 295/15* (2006.01)
*C07C 311/09* (2006.01)
(Continued)

(52) U.S. Cl.
CPC .......... *C07D 295/15* (2013.01); *C07C 311/09* (2013.01); *C10M 133/44* (2013.01);
(Continued)

(58) Field of Classification Search
CPC combination set(s) only.
See application file for complete search history.

(56) References Cited

U.S. PATENT DOCUMENTS

| | | | | |
|---|---|---|---|---|
| 10,522,827 | B2 * | 12/2019 | Young | H01M 4/383 |
| 2009/0036334 | A1 * | 2/2009 | Schwab | F03D 80/70 508/110 |

(Continued)

FOREIGN PATENT DOCUMENTS

| | | |
|---|---|---|
| CN | 102015666 A | 4/2011 |
| CN | 103553948 A | 2/2014 |

(Continued)

OTHER PUBLICATIONS

Combined Chinese Office Action and Search Report issued May 16, 2025 in Chinese Patent Application No. 2021800858701 (with unedited computer-generated English Translation), 12 pages.

(Continued)

*Primary Examiner* — Joseph D Anthony
(74) *Attorney, Agent, or Firm* — Oblon, McClelland, Maier & Neustadt, L.L.P.

(57) ABSTRACT

A compound represented by the following general formula (B1). Further disclosed is a corrosion inhibitor (B) containing one or more selected from the compound represented by the following formula (B1). Further disclosed is a lubricant composition containing an ionic liquid (A) and the corrosion inhibitor (B). The compound and the corrosion inhibitor are excellent in stability in any of a high vacuum, a low-temperature environment, a high-temperature environment, and an ordinary temperature-ordinary pressure environment, and the lubricant composition containing the corrosion inhibitor is excellent in metal corrosion resistance, solubil-
(Continued)

ity, and low evaporability. In the general formula (B1), M is an alkali metal and RB11 is an alkylene group having 1 to 19 carbon atoms.

20 Claims, 5 Drawing Sheets

(51) Int. Cl.
*C10M 133/44* (2006.01)
*C10M 135/10* (2006.01)
*C10N 20/00* (2006.01)
*C10N 30/12* (2006.01)

(52) U.S. Cl.
CPC .... *C10M 135/10* (2013.01); *C10M 2219/044* (2013.01); *C10N 2020/077* (2020.05); *C10N 2030/12* (2013.01)

(56) References Cited

U.S. PATENT DOCUMENTS

2011/0045359 A1 2/2011 Schmidt et al.
2011/0092399 A1* 4/2011 Schmidt-Amelunxen .................. C10M 169/06 508/183
2013/0102506 A1 4/2013 Yoshida et al.
2013/0137615 A1 5/2013 Hayama et al.
2016/0285130 A1* 9/2016 Meng .................. H01M 10/345
2016/0329560 A1* 11/2016 Young .................. H01M 4/383
2018/0100114 A1* 4/2018 Gao .................. C10M 169/045
2018/0100120 A1* 4/2018 Flores-Torres ....... C10M 171/02
2019/0016984 A1* 1/2019 Emett .................. C07C 51/44

FOREIGN PATENT DOCUMENTS

CN 107004912 A 8/2017
JP 2012-31275 A 2/2012
JP 2012-36294 A 2/2012
WO WO 2007/147222 A2 12/2007
WO WO 2016/077303 A1 5/2016

OTHER PUBLICATIONS

International Search Report and Written Opinion issued Mar. 1, 2022, in PCT/JP2021/048244, (with English Translation), 11 pages.
Extended European Search Report issued Apr. 22, 2024 in European Application No. 21911068.1, therein, 7 pgs.
Dorr Nicole et al: "Five-Stage Selection Procedure of Iconic Liquids for Lubrication of Steel-Steel Contacts in Space Mechanisms", Tribology Letters, Springer US, New York, vol. 67, No. 3, May 28, 2019 (May 28, 2019), pp. 1-18.
Japanese Office Action issued Oct. 1, 2024 in Japanese Patent Application No. 2020-218038 (with unedited computer-generated English translation), 4 pages.

* cited by examiner

COMPOUND, CORROSION INHIBITOR, AND LUBRICANT COMPOSITION

CROSS REFERENCE TO RELATED APPLICATIONS

This application is a National Stage entry under 35 U.S.C. § 371 of PCT/JP2021/048244, filed on Dec. 24, 2021, and claims priority to Japanese Patent Application No. 2020-218038, filed on Dec. 25, 2020, the entire contents of which are incorporated herein by reference.

TECHNICAL FIELD

The present invention relates to a compound, a corrosion inhibitor, and a lubricant composition.

BACKGROUND ART

A cosmic space has no air, different from the global environment, and therefore has no atmospheric pressure and is in an extremely high vacuum environment. In such a high vacuum, a liquid having a high vapor pressure evaporates during use, and is difficult to use in a cosmic space for a long period of time. In addition, different from the earth's surface having air, a cosmic space receives a great influence of heat emission and heat release from the sun, and therefore the surface temperature of devices to be used in a cosmic space, such as satellites, probe vehicles and lunar rover vehicles, covers a broad temperature range from below zero to high temperatures.

Therefore, these devices are exposed to severe environments different from the earth, and accordingly, in order to smoothly drive the instruments to be mounted on these devices continuously for a long period of time, a lubricant composition that can be used even in a high vacuum, or in a low-temperature environment below zero, or in a high environment at 200 to 300° C. is demanded.

A lubricant composition for lubricating instruments to be mounted on devices for space use is also required to have a reduced friction coefficient (lubricity) and to maintain the lubricity for a long period of time (low evaporability), and therefore as a base oil of the main component thereof, MAC oil (cyclopentane oil such as tris(2-octyldodecyl)cyclopentane), PFAE (perfluoroalkyl ether) or the like having a low vapor pressure is used.

However, a MAC oil has a problem in that the viscosity index is low and therefore the viscosity change relative to temperature is large. PFAE has a problem in that the lubricity thereof is insufficient.

Recently, therefore, studies of using an ionic liquid excellent in low-temperature flowability, low evaporability in high vacuum and lubricity, as a main component for lubricant compositions for space instruments are being developed (for example, see PTL 1).

CITATION LIST

Patent Literature

PTL 1: JP2012-36294A

SUMMARY OF INVENTION

Technical Problem

However, from the viewpoint of recyclability of devices for space use, it is desired that the above-mentioned instruments are, after used in a space environment, temporality returned to the earth and stored for a long period of time or overhauled, and can be again used in a space environment.

Accordingly, as a lubricant composition for space instruments, such a lubricant composition is desired that is excellent in stability and low evaporability not only in a space environment but also in an atmospheric environment after returned back to the earth, namely in an ordinary temperature and ordinary pressure environment.

However, an ionic liquid is excellent in lubricity or the like in a space environment but has a problem in that it may readily take in moisture and oxygen under atmospheric pressure to corrode some metals depending on the material.

Given the situation, a corrosion inhibitor capable of suppressing a metal corrosion behavior for an ionic liquid.

However, a corrosion inhibitor heretofore used for mineral oils has a low solubility in ionic liquids, and therefore has a problem in that it cannot be applied to ionic liquids.

In the technique described in PTL 1, a fatty acid amine salt is used as a rust inhibitor for suppressing rust generation by ionic liquids. However, the fatty acid amine salt described in PTL 1 has a problem in that it evaporates at high temperatures.

The present invention has been made in consideration of the above-mentioned problems, and its object is to provide a compound and a corrosion inhibitor excellent in stability in any of a high vacuum, a low-temperature environment, a high-temperature environment, or a normal-temperature and normal-pressure environment, and also to provide a lubricant composition containing the corrosion inhibitor and excellent in metal corrosion resistance, solubility and low evaporability.

Solution to Problem

As a result of assiduous studies, the present inventors have found that a specific compound can solve the problems, and have completed the present invention.

Specifically, the present invention provides the following [1].

[1] A compound represented by the following general formula (B1).

General Formula (B1)

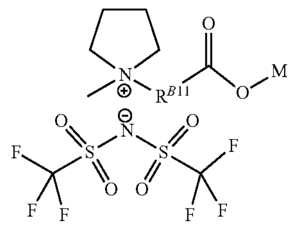

In the general formula (B1), M represents an alkali metal, $R^{B11}$ represents an alkylene group having 1 to 19 carbon atoms.

Advantageous Effects of Invention

According to the present invention, there can be provided a compound and a corrosion inhibitor excellent in stability in any of a high vacuum, a low-temperature environment, a high-temperature environment, or a normal-temperature and normal-pressure environment, and also a lubricant composition containing the corrosion inhibitor and excellent in metal corrosion resistance, solubility and low evaporability.

DESCRIPTION OF EMBODIMENTS

Figure 1:
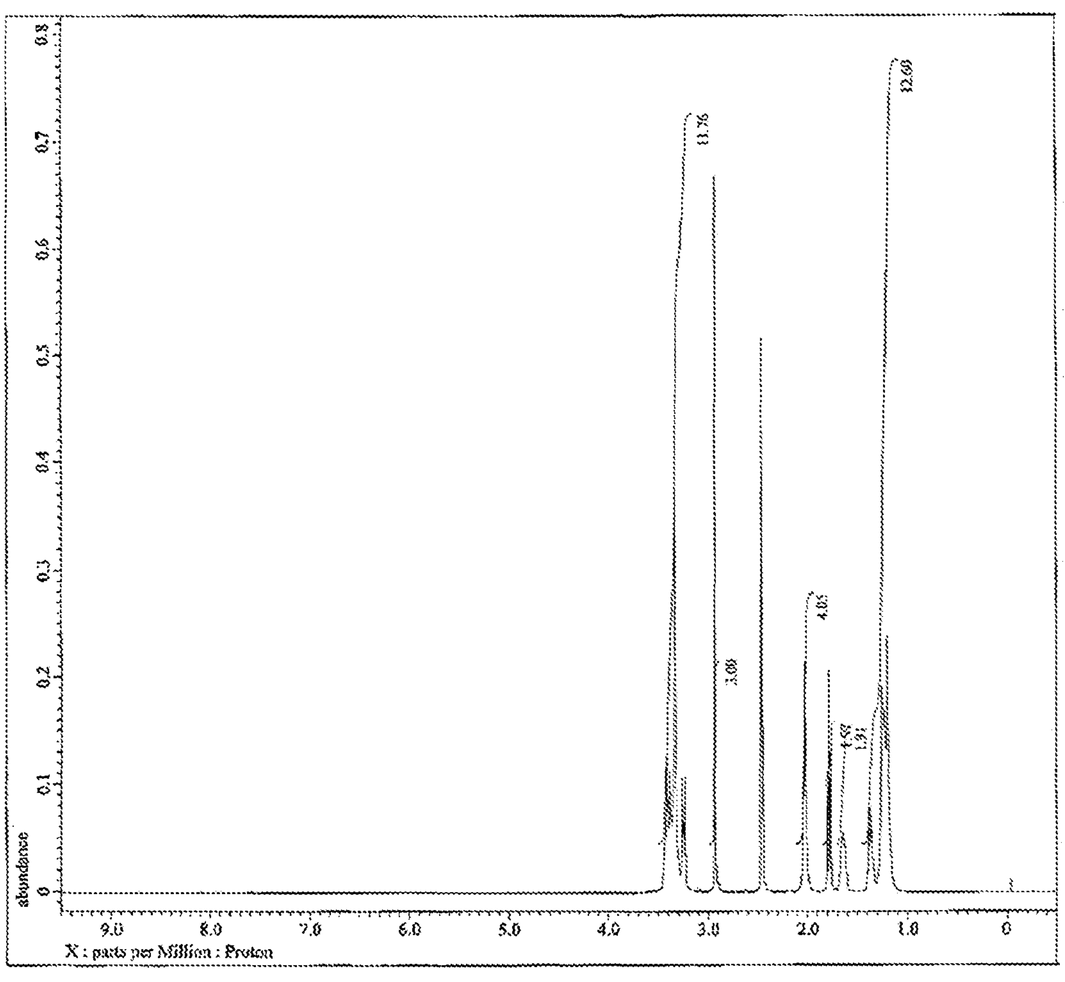
FIG. 1 is a $^1$H-NMR chart of the corrosion inhibitor (B1-1) used in Examples 1 and 2.

In the present specification, regarding the preferred numerical range (for example, a range of content etc.), the lower limit and the upper limit stepwise described can be each independently combined. For example, from a description of a lower limit "preferably 10 or more, more preferably 30 or more, even more preferably 40 or more" and a description of an upper limit "preferably 90 or less, more preferably 80 or less, even more preferably 70 or less", a range of a combination of a lower limit and an upper limit that are each independently selected, for example, "10 or more and 70 or less", "30 or more and 70 or less", and "40 or more and 80 or less", can be selected as a preferred range. Also from the same description, a range merely to define one of a lower limit or an upper limit, for example, "40 or more" or "70 or less", can be selected. Also the same shall apply to a preferred range that can be selected from a description of, for example, "preferably 10 or more and 90 or less, more preferably 30 or more and 80 or less, even more preferably 40 or more and 70 or less", or "preferably 10 to 90, more preferably 30 to 80, even more preferably 40 to 70". In addition, in the present specification, regarding the numerical range, for example, a description of "10 to 90" is the same as "10 or more and 90 or less". Descriptions of "or more", "or less", "less than" and "more than" relating to numerical ranges can be combined in any arbitrary manner.

In the present specification, for example, "(meth)acrylate" is used as a term showing both of "acrylate" and "methacrylate", and the same shall apply to the other similar terms and the same expressions.

The compound of the present embodiment is a compound represented by the following general formula (B1).

General Formula (B1)

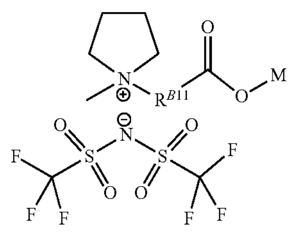

In the general formula (B1), M represents an alkali metal, $R^{B11}$ represents an alkylene group having 1 to 19 carbon atoms.

The present inventors have made assiduous studies for solving the above-mentioned problems and, as a result, have found that a compound having the cation and anion structure of the same kind as that of an ionic liquid and having a metal alkylcarboxylate in the side chain of the cation can satisfy solubility in an ionic liquid, metal corrosion resistance and stability in high-temperature environments.

On the basis of these findings, the present inventors have further made assiduous studies and have completed the present invention.

[Compound]

The compound of the present embodiment is a compound represented by the following general formula (B1).

General Formula (B1)

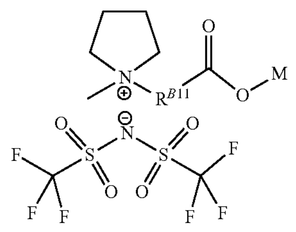

In the general formula (B1), M represents an alkali metal, $R^{B11}$ represents an alkylene group having 1 to 19 carbon atoms.

Examples of the alkali metal represented by M in the general formula (B1) include sodium and potassium. Among these, sodium is preferred from the viewpoint of the stability of the compound in high-temperature environments that, when using a differential thermal analyzer in normal pressure environments, the temperature of the compound is increased from 20° C. in a nitrogen atmosphere at a rate of 10° C./min a temperature at which the mass of the compound has decreased from the initial mass thereof by 5% by mass (5% mass reduction temperature), is higher.

$R^{B11}$ in the general formula (B1) represents an alkylene group having 1 to 19 carbon atoms, and the alkylene group can be linear or can have a branched chain. The carbon number of $R^{B11}$ is preferably 3 to 17, more preferably 5 to 15, even more preferably 7 to 12, further more preferably 8 to 10. When the carbon number of $R^{B11}$ falls within the above range, the compound can be used in a wide range of fields such as lubricant compositions and grease compositions. When the carbon number of $R^{B11}$ is 5 or more, solubility in an ionic liquid can be readily improved. Further, when the carbon number of $R^{B11}$ is 8 or more, metal corrosion resistance can be readily improved. Also when the carbon number of $R^{B11}$ is 15 or less, the 5% mass reduction temperature can be readily increased and stability in high-temperature environments can be readily improved.

The compound represented by the general formula (B1) can be synthesized, for example, according to the following synthesis method.

First, N-methylpyrrolidine, a compound represented by Br—$R^{B11}$—COO—$C_2H_5$ ($R^{B11}$ represents an alkylene group having 1 to 19 carbon atoms) and isopropanol are added to a 300-mL flask, and reacted at 50° C. to 70° C. for 7 hours to 9 hours. Ethyl acetate is added to the reaction mixture, the precipitate is washed a few times with hexane, and then dried with a vacuum pump for a few hours to give a white solid. The resultant solid is diluted in methylene chloride, and lithium bis(trifluoromethanesulfonyl)amide and water are added thereto and reacted at 10° C. to 30° C. for 0.5 hours to 2 hours. Next, the organic layer is separated, washed a few times with water, and then concentrated with an evaporator to obtain a reaction product. Methanol, water and an alkali metal hydroxide are added to the resultant reaction product, and reacted at 90° C. to 110° C. for 0.5 hours to 2 hours, and the reaction mixture is concentrated with an evaporator to obtain a compound represented by the general formula (B1).

The compound represented by the general formula (B1) can be subjected to structure analysis under the conditions described in Examples, for example, according to a $^1$H-NMR method.

[Stability in High-Temperature Environments (5% Mass Reduction Temperature)]

The 5% mass reduction temperature of the compound represented by the general formula (B1) is preferably 270° C. or higher, more preferably 300° C. or higher, even more preferably 310° C. or higher. With that, the compound has excellent stability even in high-temperature environments.

The 5% mass reduction temperature can be measured according to the method described in Examples.

<Corrosion Inhibitor (B)>

The compound represented by the general formula (B1) is excellent in metal corrosion resistance and therefore can be used as a corrosion inhibitor (B) for the lubricant composition to be mentioned hereinunder.

The corrosion inhibitor (B) contains one or more selected from the compound represented by the general formula (B1) mentioned hereinabove.

The content of the compound represented by the general formula (B1) is, based on the total amount of the corrosion inhibitor (B), preferably 60% by mass to 100% by mass, more preferably 70% by mass to 100% by mass, even more preferably 80% by mass to 100% by mass.

[Lubricant Composition]

The lubricant composition of the present embodiment contains an ionic liquid (A), and the corrosion inhibitor (B) containing one or more selected from the compound represented by the general formula (B1) mentioned above.

In the following description, the ionic liquid (A) and the corrosion inhibitor (B) may be referred to as a component (A) and a component (B), respectively.

In the lubricant composition of the present embodiment, the total content of the component (A) and the component (B) is preferably 70% by mass or more, more preferably 80% by mass or more, even more preferably 90% by mass or more, further more preferably 95% by mass or more.

In the lubricant composition of the present embodiment, the upper limit of the total content of the component (A) and the component (B) can be 100% by mass. However, in the case where the lubricant composition contains any other component than the component (A) and the component (B), the upper limit of the total content of the component (A) and the component (B) can be controlled in relation to the other component, and is preferably 99% by mass or less, more preferably 98% by mass or less.

In the lubricant composition of the present embodiment, the content of the compound represented by the general formula (B1) is, from the viewpoint of solubility in an ionic liquid (A) and from the viewpoint of more readily exhibiting the effect of metal corrosion resistance, and based on the total amount (100% by mass) of the lubricant composition, preferably 0.01% by mass or more and 10% by mass or less, more preferably 0.1% by mass or more and 10% by mass or less, even more preferably 0.1% by mass or more and 5.0% by mass or less, further more preferably 1.0% by mass or more and 3.0% by mass or less, further more preferably 1.5% by mass or more and 2.5% by mass or less.

Also in the lubricant composition of the present embodiment, the content of the corrosion inhibitor (B) is, from the viewpoint of solubility in an ionic liquid (A) and from the viewpoint of more readily exhibiting the effect of metal corrosion resistance, and based on the total amount (100% by mass) of the lubricant composition, preferably 0.01% by mass or more and 10% by mass or less, more preferably 0.1% by mass or more and 10% by mass or less, even more preferably 0.1% by mass or more and 5.0% by mass or less, further more preferably 1.0% by mass or more and 3.0% by mass or less, further more preferably 1.5% by mass or more and 2.5% by mass or less.

One alone or two or more kinds of the corrosion inhibitor (B) can be used either singly or as combined. A preferred total content in the case of using two or more kinds is the same as the above-mentioned content.

Each of the components contained in the lubricant composition of the present embodiment is described below.

<Ionic Liquid (A)>

The lubricant composition of the present embodiment contains an ionic liquid (A).

The ionic liquid is a liquid compound containing a cation and an anion.

The anion of the ionic liquid (A) preferably includes bis(trifluoromethanesulfonyl)amide.

The cation of the ionic liquid (A) preferably includes a cation represented by the following general formula (A1).

General Formula (A1)

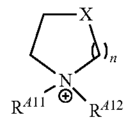

In the general formula (A1), n represents 1 or 2, X represents a methylene group or oxygen, $R^{A11}$ and $R^{A12}$ each independently represent a group selected from an alkyl group having 1 to 12 carbon atoms and optionally having an ether group, an ester group, a nitril group and a silyl group.

The carbon number of the alkyl group of $R^{A11}$ and $R^{A12}$ in the general formula (A1) is, from the viewpoint of viscosity reduction of the ionic liquid and stability improvement thereof in high-temperature environments, preferably 1 to 6, more preferably 1 to 4.

$R^{A11}$ is preferably a methyl group. $R^{A12}$ is preferably an n-butyl group or a methoxyethyl group.

Examples of the cation represented by the general formula (A1) include 1-butyl-1-methylpyrrolidinium, 1-pentyl-1-methylpyrrolidinium, 1-hexyl-1-methylpyrrolidinium, 1-heptyl-1-methylpyrrolidinium, 1-octyl-1-methylpyrrolidinium, 1-nonyl-1-methylpyrrolidinium, 1-decyl-1-methylpyrrolidinium, 1-undecyl-1-methylpyrrolidinium, 1-dodecyl-1-methylpyrrolidinium, 1-methoxymethyl-1-methylpyrrolidinium, 1-(2-methoxyethyl)-1-methylpyrrolidinium, 1-(2-methoxy-2-oxoethyl)-1-methylpyrrolidinium, 1-cyanomethyl-1-methylpyrrolidinium, 1-trimethylsilylmethyl-1-methylpyrrolidinium, 1-butyl-1-methylpiperidinium, 1-pentyl-1-methylpiperidinium, 1-hexyl-1-methylpiperidinium, 1-heptyl-1-methylpiperidinium, 1-octyl-1-methylpiperidinium, 1-nonyl-1-methylpiperidinium, 1-decyl-1-methylpiperidinium, 1-undecyl-1-methylpiperidinium, 1-dodecyl-1-methylpiperidinium, 1-methoxymethyl-1-methylpiperidinium, 1-(2-methoxyethyl)-1-methylpiperidinium, 1-(2-methoxy-2-oxoethyl)-1-methylpiperidinium, 1-cyanoethyl-1-methylpiperidinium, 1-trimethylsilylmethyl-1-methylpiperidinium, 1-butyl-1-methylmorpholinium, 1-pentyl-1-methylmorpholinium, 1-hexyl-1-methylmorpholinium, 1-heptyl-1-methylmorpholinium, 1-octyl-1-methylmorpholinium, 1-nonyl-1-methylmorpholinium, 1-decyl-1-methylmorpholinium, 1-undecyl-1-methylmorpholinium, 1-dodecyl-1-methylmorpholinium, 1-(2-methoxyethyl)-1-methylmorpholinium, 1-methoxymethyl-1-methylmorpholinium, 1-(2-methoxy-2-oxoethyl)-1-methylmorpholinium, 1-cyanomethyl-1-methylmorpholinium, and 1-trimethylsilylmethyl-1-methylmorpholinium.

Among these, from the viewpoint of viscosity reduction of the ionic liquid (A) and stability improvement thereof in high-temperature environments, preferred are 1-butyl-1-methylpyrrolidinium, 1-pentyl-1-methylpyrrolidinium, 1-hexyl-1-methylpyrrolidinium, 1-(2-methoxyethyl)-1-methylpyrrolidinium, 1-butyl-1-methylpiperidinium, 1-(2-methoxyethyl)-1-methylpiperidinium, and 1-(2-methoxyethyl)-1-methylmorpholinium, more preferred are 1-butyl-1-methylpyrrolidinium, 1-(2-methoxyethyl)-1-methylpyrrolidinium, and 1-(2-methoxyethyl)-1-methylpiperidinium, and even more preferred are 1-butyl-1-methylpyrrolidinium and 1-(2-methoxyethyl)-1-methylpyrrolidinium.

Preferably, the ionic liquid (A) contains at least one selected from a compound represented by the following general formula (A2) and a compound represented by the following general formula (A3).

General Formula (A2)

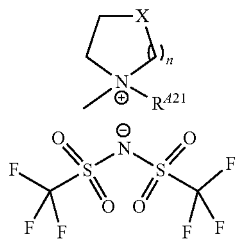

In the general formula (A2), n represents 1 or 2, X represents a methylene group or oxygen, $R^{A21}$ represents an alkyl group having 2 to 12 carbon atoms.

General Formula (A3)

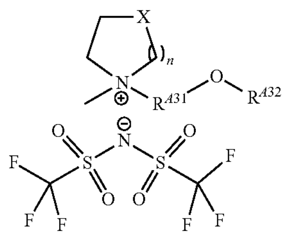

In the general formula (A3), n represents 1 or 2, X represents a methylene group or oxygen, $R^{A31}$ represents an alkylene group having 1 to 5 carbon atoms, $R^{A32}$ represents a hydrogen atom or an alkyl group having 1 to 3 carbon atoms.

In the general formula (A2), $R^{A21}$ has preferably 2 to 8 carbon atoms, more preferably 3 to 6. When $R^{A21}$ has 2 or more carbon atoms, the side chains can move freely, and the symmetricity lowers, and therefore crystallization can be suppressed and the function of the ionic liquid can be improved. When $R^{A21}$ has 12 or less carbon atoms, the side chains are prevented from being too large and the ionicity of the compound as a whole is high, and therefore the compound can be readily suppressed from being degraded by oxidation.

In the general formula (A3), $R^{A31}$ has preferably 1 to 3 carbon atoms, more preferably 1 to 2. $R^{A32}$ has preferably 1 to 2 carbon atoms. When $R^{A31}$ has 1 or more carbon atoms, the side chain can move freely, and the symmetricity lowers, and therefore crystallization can be suppressed and the function of the ionic liquid can be improved. When $R^{A31}$ has 5 or less carbon atoms, or when $R^{A32}$ has 3 or less carbon atoms, the side chain is prevented from being too large and the ionicity of the compound as a whole is high, and therefore the compound can be readily suppressed from being degraded by oxidation.

The content of the compound represented by the general formula (A2) is, based on the total amount of the ionic liquid (A), preferably 60% by mass to 100% by mass, more preferably 70% by mass to 100% by mass, even more preferably 80% by mass to 100% by mass.

Also the content of the compound represented by the general formula (A3) is, based on the total amount of the ionic liquid (A), preferably 60% by mass to 100% by mass, more preferably 70% by mass to 100% by mass, even more preferably 80% by mass to 100% by mass.

The 40° C. kinematic viscosity of the ionic liquid (A) is, from the viewpoint of low evaporability and from the viewpoint of suppressing power loss by viscosity resistance, preferably 2.0 $mm^2/s$ to 100.0 $mm^2/s$, more preferably 10.0 $mm^2/s$ to 70.0 $mm^2/s$, even more preferably 20.0 $mm^2/s$ to 40.0 $mm^2/s$.

The 100° C. kinematic viscosity of the ionic liquid (A) is, from the viewpoint of low evaporability and from the viewpoint of suppressing power loss by viscosity resistance, preferably 1.0 $mm^2/s$ to 20.0 $mm^2/s$, more preferably 2.0 $mm^2/s$ to 10.0 $mm^2/s$, even more preferably 3.0 $mm^2/s$ to 7.0 $mm^2/s$.

The viscosity index of the ionic liquid (A) is, from the viewpoint that, even in use in space environments where the temperature range greatly varies from low temperatures to high temperatures, the viscosity change can be kept small, preferably 100 or more, more preferably 120 or more, even more preferably 140 or more.

The 40° C. kinematic viscosity, the 100° C. kinematic viscosity and the viscosity index can be measured and calculated according to JIS K 2283:2000.

In the case where the ionic liquid (A) is a mixture of two or more ionic liquids, the kinematic viscosity and the viscosity index of the mixture are preferably within the above-mentioned ranges.

The pour point of the ionic liquid (A) is, from the viewpoint of suppressing increase in viscosity resistance at low temperatures, preferably 0° C. or lower, more preferably −10° C. or lower, even more preferably −20° C. or lower.

The pour point of the ionic liquid (A) can be measured according to JIS K 2269:1987.

The acid value of the ionic liquid (A) is, from the viewpoint of metal corrosion resistance, preferably 1 mg KOH/g or less, more preferably 0.5 mg KOH/g or less, even more preferably 0.3 mg KOH/g or less.

The flash point of the ionic liquid (A) is, from the viewpoint of low evaporability, preferably 200° C. or higher, more preferably 250° C. or higher, even more preferably 300° C. or higher.

The ionic concentration, as measured at 15° C., of the ionic liquid (A) is preferably 1.0 mol/$dm^3$ or more, more preferably 1.5 mol/$dm^3$ or more, even more preferably 2.0 mol/$dm^3$ or more.

Here, the ionic concentration is a value of the ionic liquid calculated as [density measured at 15° C. (g/cm 3)/molecular weight Mw (g/mol)]×1000. When the ionic concentration of the ionic liquid (A) is 1.0 mol/$dm^3$ or more, low evaporability and stability in high-temperature environments can be improved more.

The molecular weight of the ionic liquid (A) is preferably 410 or more and 570 or less, more preferably 410 or more and 470 or less, even more preferably 420 or more and 440 or less. When the molecular weight of the ionic liquid (A) falls within the range, the charge density and the cation alkyl chain length each can fall within a suitable range, and therefore if so, viscosity reduction of the ionic liquid and stability in high temperature environments thereof can be improved.

In the lubricant composition of the present embodiment, the content of the ionic liquid (A) is, though not specifically limited but from the viewpoint of more readily exhibiting the advantageous effects of the present invention, preferably 60% by mass to 99.5% by mass, more preferably 70% by mass to 99.0% by mass, even more preferably 80% by mass to 98.5% by mass, based on the total amount (100% by mass) of the lubricant composition.

The lubricant composition of the present embodiment can contain any other component (for example, ethyl acetate) than the above-mentioned ionic liquid (A). From the viewpoint of sufficiently exhibiting the advantageous effects of the present invention, the content of the ionic liquid (A) is, based on the total amount of the ionic liquid, preferably 50% by mass or more, more preferably 70% by mass or more, even more preferably 90% by mass or more, further more preferably 100% by mass.

The ratio of the content of the compound represented by the general formula (B1) to the content of the ionic liquid (A), (B1/A) is, by mass, preferably 0.0005 or more and 0.15 or less, more preferably 0.001 or more and 0.111 or less, even more preferably 0.005 or more and 0.08 or less. When (B1/A) is 0.0005 or more, metal corrosion resistance can be readily sufficient. When (B1/A) is 0.15 or less, solubility in the ionic liquid (A) can be readily sufficient.

<Other Component>

The lubricant composition of the present embodiment can contain, as needed, any other component than the above-mentioned components within a range not detracting from the advantageous effects of the present invention.

Examples of the other component include a viscosity index improver.

One kind alone or two or more kinds thereof can be used either singly or as combined.

—Viscosity Index Improver—

When the lubricant composition of the present embodiment contains a viscosity index improver, the viscosity index of the lubricant composition can be improved. With that, even in use in space environments where the temperature range greatly varies from low temperatures to high temperatures, the viscosity change can be kept small.

Examples of the viscosity index improver include polymers soluble in the ionic liquid, such as non-dispersant-type poly(meth)acrylates and dispersant-type poly(meth)acrylates.

One kind alone or two or more kinds thereof can be used either singly or as combined.

The mass-average molecular weight (Mw) of the viscosity index improver is generally 5,000 to 1,000,000, preferably 6,000 to 100,000, more preferably 10,000 to 50,000, and can be appropriately set depending on the kind of the polymer.

In the present specification, the mass-average molecular weight (Mw) of each component is a standard polyethylene-equivalent value measured according to a gel permeation chromatography (GPC) method.

The content of the other component mentioned above can be appropriately controlled within a range not detracting from the advantageous effects of the present invention, and each individual component is, based on the total amount (100% by mass) of the lubricant composition, generally 0.001% by mass to 15% by mass, preferably 0.005% by mass to 10% by mass, more preferably 0.01% by mass to 7% by mass, even more preferably 0.03% by mass to 5% by mass.

In the present description, the additive as the other component mentioned above can be blended with any other component in the form of a solution diluted and dissolved in a part of the ionic liquid (A) in consideration of the handleability and the solubility thereof in the ionic liquid (A), for example. In such a case, in the present description, the content of the additive as the other component means the effective ingredient-equivalent (resin-equivalent) content thereof excluding the diluent.

[Physical Data of Lubricant Composition]

<40° C. Kinematic Viscosity, 100° C. Kinematic Viscosity, and Viscosity Index>

The 40° C. kinematic viscosity of the lubricant composition of the present embodiment is, from the viewpoint of low evaporability and from the viewpoint of suppressing power loss by viscosity resistance, preferably 2.0 $mm^2$/s to 100.0 $mm^2$/s, more preferably 10.0 $mm^2$/s to 70.0 $mm^2$/s, even more preferably 20.0 $mm^2$/s to 50.0 $mm^2$/s.

The 100° C. kinematic viscosity of the lubricant composition of the present embodiment is, from the viewpoint of low evaporability and from the viewpoint of suppressing power loss by viscosity resistance, preferably 1.0 $mm^2$/s to 20.0 $mm^2$/s, more preferably 2.0 $mm^2$/s to 15.0 $mm^2$/s, even more preferably 3.0 $mm^2$/s to 10.0 $mm^2$/s.

The viscosity index of the lubricant composition of the present embodiment is, from the viewpoint that, even in use in space environments where the temperature range greatly varies from low temperatures to high temperatures, the viscosity change can be kept small, preferably 100 or more, more preferably 120 or more, even more preferably 140 or more.

The 40° C. kinematic viscosity, the 100° C. kinematic viscosity and the viscosity index can be measured and calculated according to JIS K 2283:2000.

<Solubility (Appearance)>

Preferably, the corrosion inhibitor (B) dissolves in the ionic liquid (A) to be colorless and transparent. This can be judged according to the method described in Examples.

<Low Evaporability (Evaporation Amount)>

The evaporation amount is preferably less than 0.1% by mass. This can be measured according to the method described in Examples.

<Metal Corrosion Resistance>

Regarding metal corrosion resistance, preferably, no corrosion is found in judgement according to the method described in Examples.

[Use of Lubricant Composition]

The lubricant composition of the present embodiment is excellent in metal corrosion resistance, solubility and low evaporability not only in a high vacuum, in a low-temperature environment and in a high-temperature environment but also in a normal-temperature normal-pressure environment, and can be therefore favorably used for instruments to be mounted on devices for use in a cosmic space, such as satellites, probe vehicles and lunar rover vehicles. Also the lubricant composition of the present embodiment is excellent in use in a high vacuum, and is therefore favorably used, for example, for production devices for semiconductors, flat panel displays of liquid crystals or organic EL, solar cell panels, and the like.

The lubricant composition of the present embodiment is favorable for use as a lubricant composition for devices for use in a cosmic space, but can be used in other applications.

[Production Method for Lubricant Composition]

The present embodiment provides a production method for a lubricant composition, including a step of mixing an ionic liquid (A) and a compound represented by the following general formula (B1).

General Formula (B1)

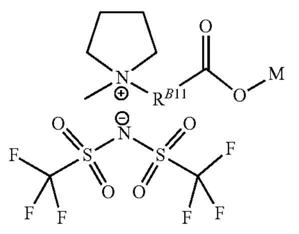

In the general formula (B1), M represents an alkali metal, $R^{B11}$ represents an alkylene group having 1 to 19 carbon atoms.

The method of mixing the components is not specifically limited, and is, for example, a step of adding a compound represented by the following general formula (B1) to an ionic liquid (A) and the mixing them.

The production method can further include a step of adding the other component mentioned above.

[Grease Composition]

The lubricant composition of the present embodiment can also be used as a grease composition containing the ionic liquid (A), the corrosion inhibitor (B) and a thickener.

A cosmic space is a micro-gravity environment, in which, therefore, a gravity-supply type method for lubricant supply cannot be used. However, by applying the lubricant composition of the present embodiment to a grease composition, lubricity can be maintained without supply during use of lubricant.

As the thickener for the grease composition, cellulose nanofibers can preferably be used. The ionic liquid (A) and cellulose nanofibers are both hydrophilic, and therefore the ionic liquid (A) and the corrosion inhibitor (B) can be sustained with good affinity in cellulose nanofibers.

The grease composition can contain any other component than the component (A) and the component (B) within a range not detracting from the advantageous effects of the present invention.

<Nanofibers>

The nanofibers to be contained in the grease composition of the present embodiment are preferably one or more kind selected from cellulose nanofibers and hydrophilic modified cellulose nanofibers.

In the grease composition containing nanofibers, the nanofibers uniformly disperse in the grease composition to form a higher-order structure. The nanofibers are excellent in mechanical stability, and therefore the higher-order structure of such nanofibers can be stable to shear. Consequently, the shear stability of the grease composition increases to improve the grease leakage prevention performance thereof.

Also even when the content of nanofibers is small, the proportion of the ionic liquid (A) in the grease composition can be increased by controlling the worked penetration of the grease composition to fall within an appropriate range. Consequently, lubricity of the grease composition increases and wear resistance thereof can be readily improved.

(Cellulose Nanofibers)

A cellulose nanofiber means a fibrous substance having a thickness of 500 nm or less, produced by defibrillating vegetable fibers on a nano-level, and is differentiated from a flaky substance, a powdery substance and a granular substance.

A lignocellulose can also be used as a raw material for cellulose nanofibers. A lignocellulose is a composite hydrocarbon polymer constituting a cell wall of a plant, and is known to be composed of mainly a polysaccharide, cellulose or hemicellulose, and an aromatic polymer, lignin.

Cellulose to constitute cellulose nanofibers can be one or more selected from a lignocellulose and an acetylated lignocellulose. The cellulose nanofiber can contain one or more selected from a hemicellulose and a lignin. Further, the cellulose to constitute the cellulose nanofiber can chemically bond to one or more selected from a hemicellulose and a lignin.

The polymerization degree of cellulose to constitute cellulose nanofibers is preferably 50 to 3,000, more preferably 100 to 1,500, even more preferably 150 to 1,000, further more preferably 200 to 800.

In the present description, the polymerization degree of cellulose means a value measured according to a viscosity method.

(Hydrophilic Modified Cellulose Fibers)

A hydrophilic modified cellulose fiber is produced by modification treatment of a cellulose nanofiber within a range capable of maintaining hydrophilicity.

Specific examples of modification treatment include esterification such as acetylation, phosphorylation, urethanation, carbamidation, etherification, carboxymethylation, TEMPO (2,2,6,6-tetramethylpiperidine-1-oxyl radical) oxidation, and periodic acid oxidation.

The modified cellulose nanofibers for use in the present invention can be modified by only one of such modification treatments, or by two or more thereof.

One embodiment of the present invention provides the following [1] to [7].

[1] A compound represented by the following general formula (B1):

General Formula (B1)

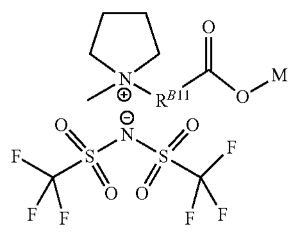

wherein M represents an alkali metal, $R^{B11}$ represents an alkylene group having 1 to 19 carbon atoms, in the general formula (B1).

[2] A corrosion inhibitor containing one or more selected from the compound of the above [1].

[3] A lubricant composition containing an ionic liquid (A) and the corrosion inhibitor (B) of the above [2].

[4] The lubricant composition according to the above [3], wherein the ionic liquid (A) contains a cation represented by the following general formula (A1):

General Formula (A1)

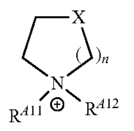

wherein n represents 1 or 2, X represents a methylene group or oxygen, $R^{A11}$ and $R^{A12}$ each independently represent a group selected from an alkyl group having 1 to 12 carbon atoms and optionally having an ether group, an ester group, a nitril group and a silyl group, in the general formula (A1).

[5] The lubricant composition according to the above [3] or [4], wherein the ionic liquid (A) contains at least one selected from a compound represented by the following general formula (A2) and a compound represented by the following general formula (A3):

General Formula (A2)

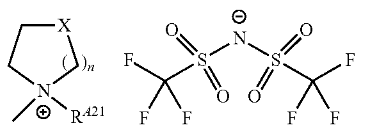

wherein n represents 1 or 2, X represents a methylene group or oxygen, $R^{A21}$ represents an alkyl group having 2 to 12 carbon atoms, in the general formula (A2), General Formula (A3)

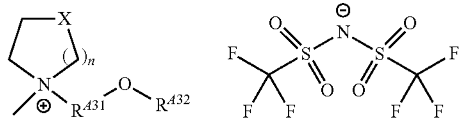

wherein n represents 1 or 2, X represents a methylene group or oxygen, $R^{A31}$ represents an alkylene group having 1 to 5 carbon atoms, $R^{A32}$ represents a hydrogen atom or an alkyl group having 1 to 3 carbon atoms, in the general formula (A3).

[6] The lubricant composition according to any one of the above [3] to [5], wherein the content of the compound represented by the general formula (B1) is, based on the total amount of the lubricant composition, 0.1% by mass or more and 10% by mass or less.

[7] The lubricant composition according to any one of the above [3] to [6], wherein the ratio of the content of the compound represented by the general formula (B1) to the content of the ionic liquid (A), (B1/A) is, as a ratio by mass, 0.0005 or more and 0.15 or less.

EXAMPLES

The present invention is described more specifically with reference to the following Examples, but the invention is not limited to the following Examples.

The structure of the individual corrosion inhibitor to be mentioned below was analyzed according to the following method.

[NMR Structure Analysis]

Figure 2:
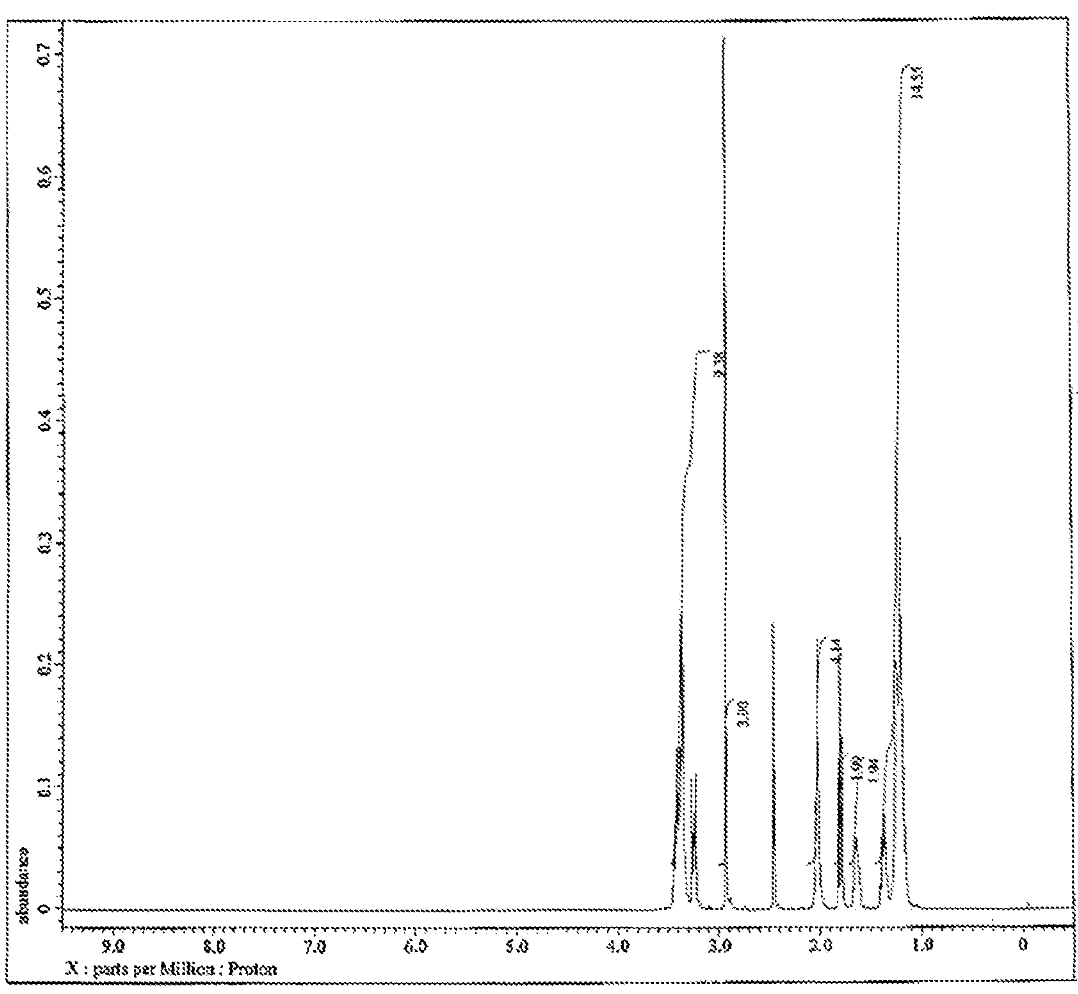
FIG. 2 is a $^1$H-NMR chart of the corrosion inhibitor (B1-2) used in Example 3.
Figure 3:
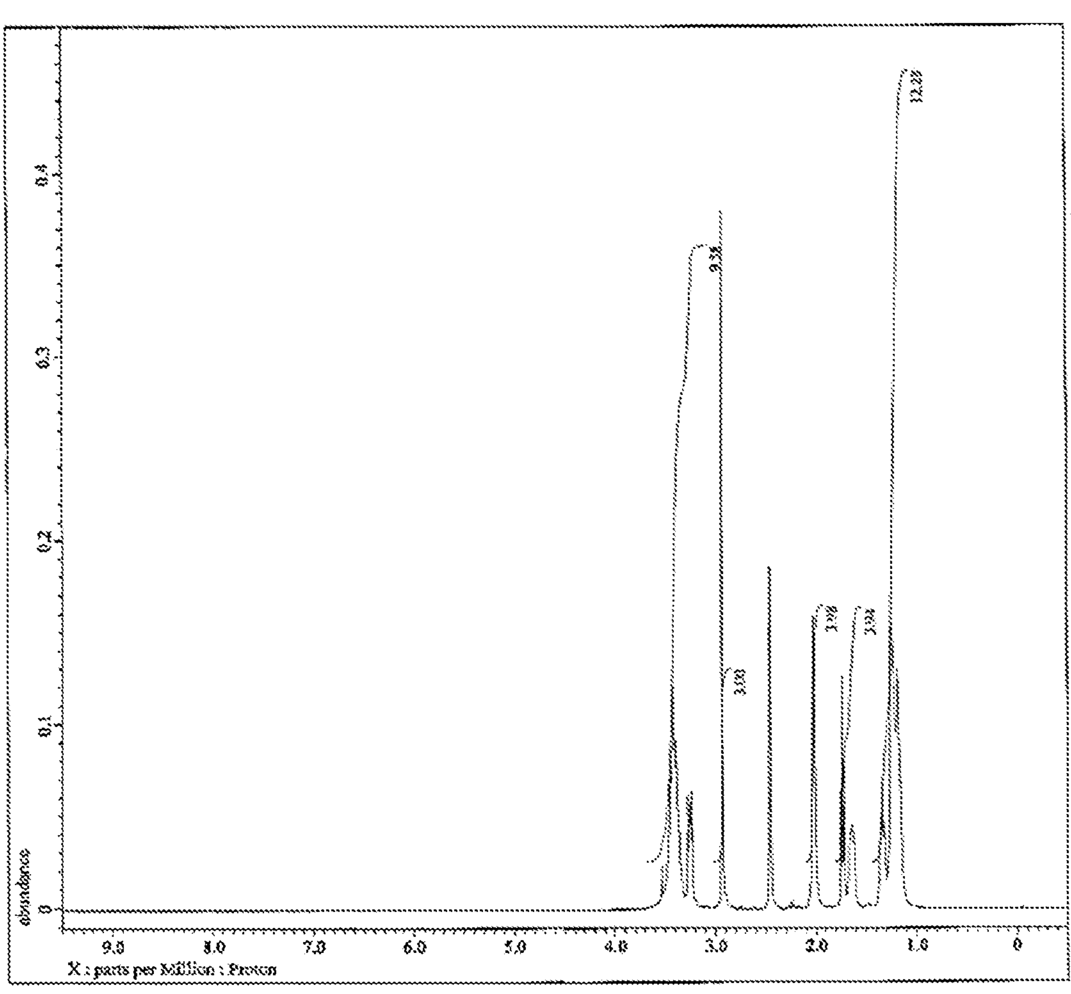
FIG. 3 is a $^1$H-NMR chart of the corrosion inhibitor (B1-3) used in Example 4.
Figure 4:
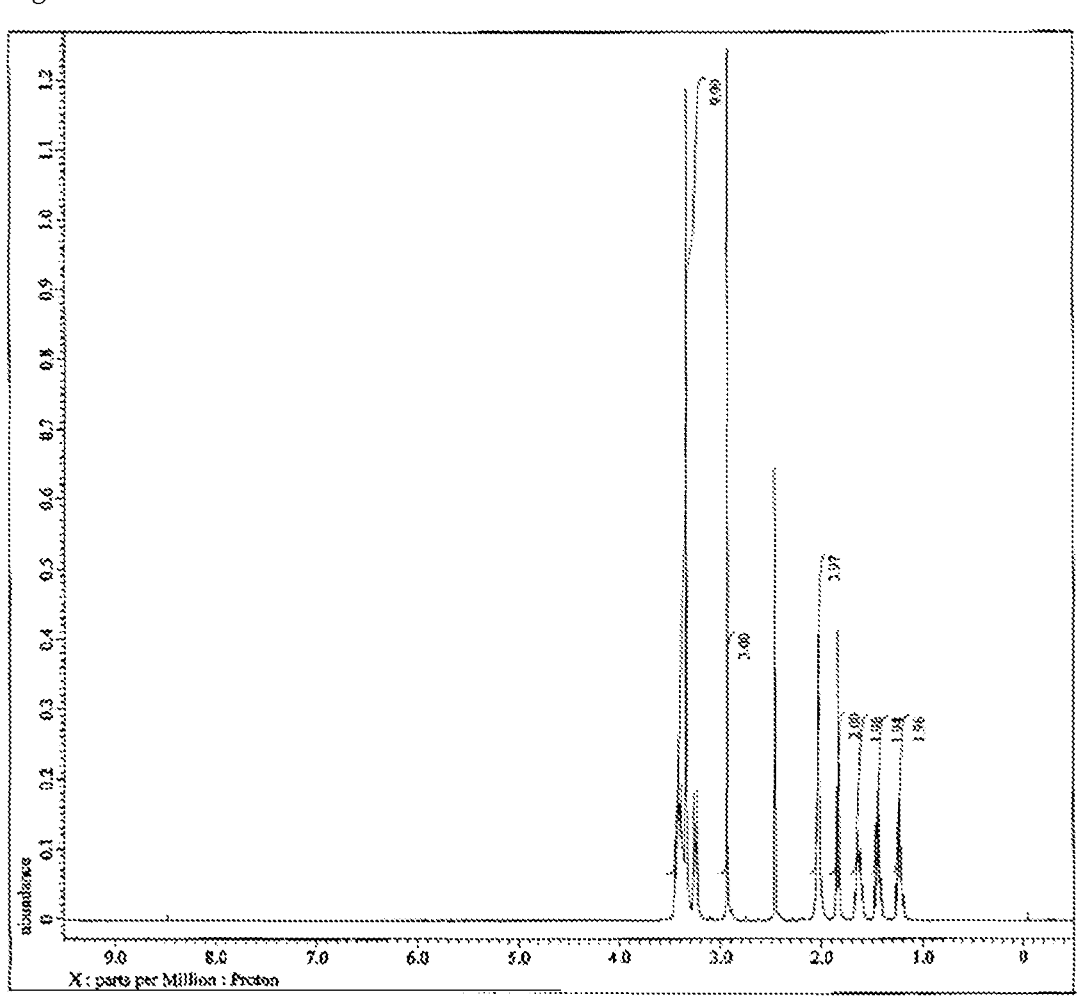
FIG. 4 is a $^1$H-NMR chart of the corrosion inhibitor (B1-4) used in Example 5.
Figure 5:
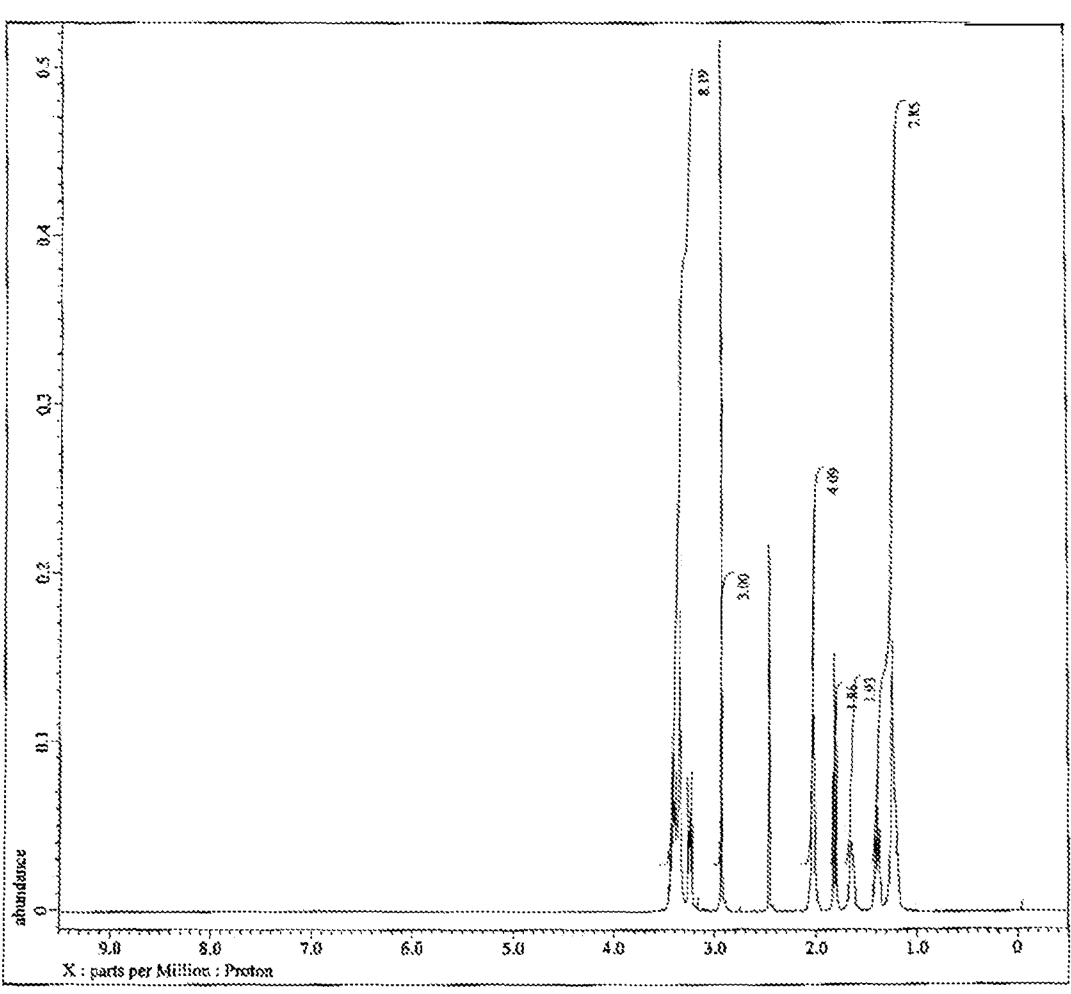
FIG. 5 is a $^1$H-NMR chart of the corrosion inhibitor (B1-5) used in Example 6.

Corrosion inhibitors (B1-1) to (B1-5) to be mentioned below were analyzed according to a $^1$H-NMR method. The resultant $^1$H-NMR charts are shown in FIG. 1 to FIG. 5.

Name of Apparatus: JNM-ECZ400S (by JEOL Ltd.)

Measurement Temperature: 20° C.

Standard Substance: DMSO-D6

[Synthesis and Procurement of Corrosion Inhibitor (B)]

Corrosion inhibitors (B1-1) to (B1-5) and a corrosion inhibitor (B2-2) were synthesized according to the method mentioned below. Corrosion inhibitors (B2-1) and (B2-3) were procured.

<Corrosion Inhibitor (B1-1)>

Corrosion Inhibitor (B1-1)

First, N-methylpyrrolidine (2.44 g, 28.6 mmol), ethyl 10-bromodecanoate (8.80 g, 31.5 mmol) and isopropanol (20 mL) were put into a 300-mL flask, and reacted at 60° C. for 8 hours. Ethyl acetate (100 mL) was added to the reaction mixture, the precipitate was washed a few times with hexane, and then dried with a vacuum pump for a few hours to obtain 9.5 g of a white solid. The resultant white solid was diluted with methylene chloride (100 mL), and lithium bis(trifluoromethanesulfonyl)amide (8.21 g, 28.6 mmol) and water (100 mL) were added and reacted at 20° C. for 1 hour. Next, the organic layer was separated, washed a few times with water, and then concentrated with an evaporator to obtain 14.1 g of a reaction product. Methanol (16 mL), water (2 mL) and sodium hydroxide (1.00 g, 25.0 mmol) were added to the resultant reaction product and reacted at 100° C. for 1 hour, and the reaction mixture was concentrated with an evaporator to obtain a corrosion inhibitor (B1-1).

The resultant corrosion inhibitor (B1-1) was 13.57 g and 24.3 mmol. The 5% mass reduction temperature of the corrosion inhibitor (B1-1) was 317° C. The structure of the corrosion inhibitor (B1-1) is shown as a structural formula (B1-1).

Structural Formula (B1-1)

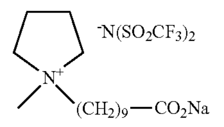

<Corrosion Inhibitor (B1-2)>

Corrosion Inhibitor (B1-2)

A corrosion inhibitor (B1-2) was synthesized according to the same method as above, except that ethyl 11-bromoundecanoate (9.24 g, 31.5 mmol) was used in place of ethyl 10-bromodecanoate in synthesis of the corrosion inhibitor (B1-1).

The resultant corrosion inhibitor (B1-2) was 13.63 g and 23.8 mmol. The 5% mass reduction temperature of the corrosion inhibitor (B1-2) was 314° C. The structure of the corrosion inhibitor (B1-2) is shown as a structural formula (B1-2).

Structural Formula (B1-2)

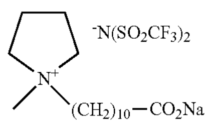

<Corrosion Inhibitor (B1-3)>
Corrosion Inhibitor (B1-3)

A corrosion inhibitor (B1-3) was obtained according to the same method as above, except that potassium hydroxide (1.40 g, 25.0 mmol) was used in place of sodium hydroxide in synthesis of the corrosion inhibitor (B1-1).

The resultant corrosion inhibitor (B1-3) was 13.51 g and 23.5 mmol. The 5% mass reduction temperature of the corrosion inhibitor (B1-3) was 280° C. The structure of the corrosion inhibitor (B1-3) is shown as a structural formula (B1-3).

Structural Formula (B1-3)

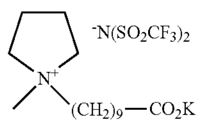

<Corrosion Inhibitor (B1-4)>
Corrosion Inhibitor (B1-4)

A corrosion inhibitor (B1-4) was obtained according to the same method as above, except that ethyl 6-bromohexanoate (7.03 g, 31.5 mmol) was used in place of ethyl 10-bromodecanoate in synthesis of the corrosion inhibitor (B1-1).

The resultant corrosion inhibitor (B1-4) was 12.57 g and 25.0 mmol. The 5% mass reduction temperature of the corrosion inhibitor (B1-4) was 291° C. The structure of the corrosion inhibitor (B1-4) is shown as a structural formula (B1-4).

Structural Formula (B1-4)

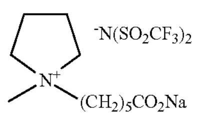

<Corrosion Inhibitor (B1-5)>
Corrosion Inhibitor (B1-5)

A corrosion inhibitor (B1-5) was obtained according to the same method as above, except that ethyl 8-bromooctanoate (7.91 g, 31.5 mmol) was used in place of ethyl 10-bromodecanoate in synthesis of the corrosion inhibitor (B1-1).

The resultant corrosion inhibitor (B1-5) was 13.16 g and 24.8 mmol. The 5% mass reduction temperature of the corrosion inhibitor (B1-5) was 318° C. The structure of the corrosion inhibitor (B1-5) is shown as a structural formula (B1-5).

Structural Formula (B1-5)

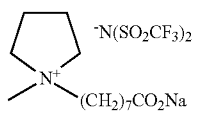

<Corrosion Inhibitor (B2-1)>
Corrosion Inhibitor (B2-1): Disodium Sebacate

Disodium sebacate (by Tokyo Chemical Industry Co., Ltd.) was procured and used as a corrosion inhibitor (B2-1). The 5% mass reduction temperature of the corrosion inhibitor (B2-1) was 381° C. The structure of the corrosion inhibitor (B2-1) is shown as a structural formula (B2-1).

Structural Formula (B2-1)

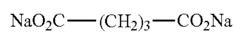

$NaO_2C—(CH_2)_3—CO_2Na$

<Corrosion Inhibitor (B2-2)>
Corrosion Inhibitor (B2-2): bis(tetramethylammonium) decanedioate Decanedioic acid (27.7 g, 0.137 mol) and tetramethylammonium hydroxide (about 25% aqueous solution, 100 g, 0.274 mol) were put in a 500-mL flask, and reacted at room temperature (20° C.) for 1 hour. The reaction mixture was concentrated with a rotary evaporator, and the resultant solid was dried for a few hours with a vacuum pump to obtain a corrosion inhibitor (B2-2).

The resultant corrosion inhibitor (B2-2) was 47.4 g and 0.136 mmol. The 5% mass reduction temperature of the corrosion inhibitor (B2-2) was 200° C. The structure of the corrosion inhibitor (B2-2) is shown as a structural formula (B2-2).

Structural Formula (B2-2)

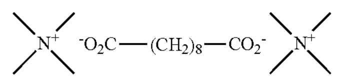

<Corrosion Inhibitor (B2-3)>
Corrosion Inhibitor (B2-3):

Trade name, Cheleslite T (trade name, by Chelest Corporation) was procured and used as a corrosion inhibitor (B2-3). The 5% mass reduction temperature of the corrosion inhibitor (B2-3) was 130° C.

The resultant corrosion inhibitors were evaluated as follows. The results are shown in Table 1.

[Evaluation of Stability in High-Temperature Environments (5% Mass Reduction Temperature)]

The compounds of the corrosion inhibitors (B1-1) to (B1-5) and the corrosion inhibitors (B2-1) to (B2-3) were individually tested using a differential thermal analyzer in normal pressure environments. Each compound was heated in a nitrogen atmosphere from 20° C. at a rate of 10° C./min to measure the temperature at which the mass of the compound decreased from the initial mass thereof by 5% by mass (5% mass reduction temperature).

TABLE 1

| Corrosion Inhibitor | 5% mass reduction temperature (° C.) |
|---|---|
| Corrosion Inhibitor (B1-1) | 317 |
| Corrosion Inhibitor (B1-2) | 314 |
| Corrosion Inhibitor (B1-3) | 280 |
| Corrosion Inhibitor (B1-4) | 291 |
| Corrosion Inhibitor (B1-5) | 318 |
| Corrosion Inhibitor (B2-1) | 381 |
| Corrosion Inhibitor (B2-2) | 200 |
| Corrosion Inhibitor (B2-3) | 130 |

As known from Table 1, the corrosion inhibitors (B1-1) to (B1-5) satisfying all the constitution of the present invention had a sufficiently high 5% mass reduction temperature, 270° C. or higher, and are known to be stable even in high-temperature environments.

On the other hand, the 5% mass reduction temperature of the corrosion inhibitor (B2-1) was 270° C. or higher, but the 5% mass reduction temperature of the corrosion inhibitors (B2-2) and (B2-3) was lower than 270° C., which was low. Accordingly, there is a probability that the corrosion inhibitors (B2-2) and (B2-3) could not be used in space environments of high-temperature environments.

Next, using the corrosion inhibitors (B1-1) to (B1-5) and the corrosion inhibitors (B2-1) to (B2-3), lubricant compositions were produced according to the method described below.

Physical properties of the lubricant compositions were measured or calculated according to the following methods.

[40° C. Kinematic Viscosity, 100° C. Kinematic Viscosity, and Viscosity Index]

The 40° C. kinematic viscosity, the 100° C. kinematic viscosity, and the viscosity Index of the lubricant compositions and the ionic liquid (A) were measured or calculated according to JIS K 2283:2000.

[Pour Point]

The pour point of the ionic liquid (A) was measured according to JIS K2269:1987.

[Density]

The density at 15° C. of the ionic liquid (A) was measured according to JIS K 2249-1:2011.

[5% Mass Reduction Temperature]

In the same manner as that for the corrosion inhibitor mentioned above, the temperature at which the mass has decreased by 5% by mass from the initial mass (5% mass reduction temperature) of the ionic liquids (A-1) and (A-2) was measured.

[Synthesis of Ionic Liquid (A)]

Ionic liquids (A-1) and (A-2) were synthesized according to the method mentioned below.

<Ionic Liquid (A-1)>

Ionic Liquid (A-1): 1-butyl-1-methylpyrrolidinium bis(trifluoromethanesulfonyl)amide 1-Methylpyrrolidine (50 g, 0.587 mol) and 70 mL of 2-propanol were put into a 1-L flask in a nitrogen atmosphere. 1-Bromobutane (96 g, 0.704 mol) was dropwise added thereto, then heated up to 40° C. and reacted for 6 hours. After the reaction, this was recrystallized with ethyl acetate, and filtered, and the resultant crystal was washed a few times with ethyl acetate. Subsequently, this was dried for a few hours at 40° C. while depressurized down to 1 mmHg or less via a vacuum pump to obtain 1-butyl-1-methylpyrrolidinium bromide (halide) (113 g, 0.509 mol).

Next, the above halide (113 g, 0.509 mol) and 110 mL of pure water were arranged in a 1-L flask, and an aqueous solution prepared by dissolving lithium bis(trifluoromethanesulfonyl)imide (151 g, 0.526 mol) in 150 mL of pure water was dropwise added thereto. The reaction mixture was stirred at room temperature (20° C.) for about 1 hour, then transferred to a 1-L separatory funnel, 230 mL of methylene chloride was added thereto for extraction, and the collected methylene chloride solution was washed a few times with pure water. After the washing, about 1 to 2 ml of the aqueous layer was collected, and reacted with about 1 mL of aqueous 0.5 M silver nitrate solution to confirm the presence or absence of precipitates. In the case where a white precipitate is detected, this means that a bromide ion could not be completely removed, and therefore, washing was repeated until disappearance of the precipitate. After completely water-washed, this was concentrated with a rotary evaporator, and a small amount of active charcoal was added thereto and stirred at room temperature (20° C.) for one day. The mixture was led to pass through a neutral alumina column, and stirred with heating (60° C., 4 hours) with a vacuum pump to obtain the ionic liquid (A-1).

The resultant ionic liquid (A-1) was 212 g, 0.502 mol. The ionic liquid (A-1) had a 40° C. kinematic viscosity of 25.08 $mm^2/s$, a 100° C. kinematic viscosity of 5.662 $mm^2/s$, a viscosity index of 177, a pour point of lower than −50° C., a density of 1.401 (15° C.), and a 5% mass reduction temperature of 380° C. The structure of the ionic liquid (A-1) is shown as a structural formula (A-1).

Structural Formula (A-1)

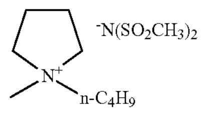

<Ionic Liquid (A-2)>

Ionic Liquid (A-2): 1-(2-methoxyethyl)-1-methylpyrrolidinium bis(trifluoromethanesulfonyl)amide In the same manner as above, except that 2-iodoethyl methyl ether (131 g, 0.705 mol) was used in place of 1-bromobutane in synthesis of the ionic liquid (A-1), 1-(2-methoxyethyl)-1-methylpyrrolidinium iodide (146 g, 0.538 mol) was produced.

Also in the same manner as above, except that the resultant 1-(2-methoxyethyl)-1-methylpyrrolidinium iodide (146 g, 0.538 mol) was used in place of 1-butyl-1-methylpyrrolidinium bromide in synthesis of the ionic liquid (A-1), the ionic liquid (A-2) was produced.

The resultant ionic liquid (A-2) was 212 g, 0.500 mol. The ionic liquid (A-2) had a 40° C. kinematic viscosity of 21.34 $mm^2/s$, a 100° C. kinematic viscosity of 5.170 $mm^2/s$, a viscosity index of 187, a pour point of lower than −50° C., a density of 1.462 (15° C.), and a 5% mass reduction temperature of 388° C. The structure of the ionic liquid (A-2) is shown as a structural formula (A-2).

Structural Formula (A-2)

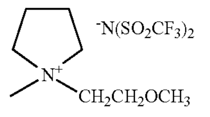

Preparation of Examples 1 to 6, and Comparative Examples 1 to 5

The following components were weighed each in an amount shown in Table 2 and Table 3 and fully mixed to produce lubricant compositions.

Details of each of the components used in Examples 1 to 6 and Comparative Examples 1 to 5 are as shown below.

The resultant lubricant compositions were evaluated as follows. The results are shown in Table 2 and Table 3.

[Evaluation of Solubility (Appearance)]

In 3 hours after the preparation, the appearance of each lubricant composition at 20° C. and in normal pressure environments was observed and judged as follows.

Transparent: The corrosion inhibitor (B) dissolved in the ionic liquid (A) to be colorless transparent.

Insoluble: The corrosion inhibitor (B) did not dissolve in the ionic liquid (A).

[Evaluation of Low Evaporability (Evaporation Amount)]

100 g of each lubricant composition and a stirrer were put in a flask, depressurized down to 1 mmHg or less via a vacuum pump, and stirred in an oil bath at 120° C. for 24 hours. After cooled to room temperature, the mass of the residual sample was measured, and the proportion of the reduced mass (% by mass) was referred to as an evaporation amount.

[Evaluation of Metal Corrosion Resistance]

A SUS440C plate cut in a long strip form was immersed in a solution prepared by mixing 10 g of distilled water and 10 g of each lubricant composition. The temperature of the solution was set at 60° C., and the SUS440C plate was immersed for 7 days, and thereafter the appearance of the SUS440C plate was observed. When samples having a discolored (rusted) dark brown or black surface were observed, they were considered to be corroded.

A: No corrosion.

B: Surface corroded.

TABLE 2

| | | | Example | | | | | |
|---|---|---|---|---|---|---|---|---|
| | | | 1 | 2 | 3 | 4 | 5 | 6 |
| Ionic Liquid | Ionic Liquid (A-1) | mass % | 98 | — | — | 98 | 98 | 98 |
| | Ionic Liquid (A-2) | mass % | — | 98 | 98 | — | — | — |
| Corrosion Inhibitor | Corrosion Inhibitor (B1-1) | mass % | 2 | 2 | — | — | — | — |
| | Corrosion Inhibitor (B1-2) | mass % | — | — | 2 | — | — | — |
| | Corrosion Inhibitor (B1-3) | mass % | — | — | — | 2 | — | — |
| | Corrosion Inhibitor (B1-4) | mass % | — | — | — | — | 2 | — |
| | Corrosion Inhibitor (B1-5) | mass % | — | — | — | — | — | 2 |
| | Corrosion Inhibitor (B2-1) | mass % | — | — | — | — | — | — |
| | Corrosion Inhibitor (B2-2) | mass % | — | — | — | — | — | — |
| | Corrosion Inhibitor (B2-3) | mass % | — | — | — | — | — | — |
| | Total | mass % | 100 | 100 | 100 | 100 | 100 | 100 |
| Physical Data | 40° C. Kinematic Viscosity | $mm^2/s$ | 27.15 | 23.33 | 23.91 | 28.38 | 28.48 | 27.93 |
| | 100° C. Kinematic Viscosity | $mm^2/s$ | 5.975 | 5.539 | 5.566 | 6.107 | 6.055 | 6.039 |
| | Viscosity Index | — | 175 | 190 | 184 | 171 | 167 | 172 |
| Evaluation Item | Solubility (appearance) | — | transparent | transparent | transparent | transparent | transparent | transparent |
| | Low Evaporability (evaporation amount) | mass % | <0.1 | <0.1 | <0.1 | <0.1 | <0.1 | <0.1 |
| | Metal Corrosion Resistance | — | A | A | A | A | A | A |

TABLE 3

| | | | Comparative Example | | | | |
|---|---|---|---|---|---|---|---|
| | | | 1 | 2 | 3 | 4 | 5 |
| Ionic Liquid | Ionic Liquid (A-1) | mass % | 100 | — | 98 | 98 | 98 |
| | Ionic Liquid (A-2) | mass % | — | 100 | — | — | — |
| Corrosion Inhibitor | Corrosion Inhibitor (B1-1) | mass % | — | — | — | — | — |
| | Corrosion Inhibitor (B1-2) | mass % | — | — | — | — | — |
| | Corrosion Inhibitor (B1-3) | mass % | — | — | — | — | — |
| | Corrosion Inhibitor (B1-4) | mass % | — | — | — | — | — |
| | Corrosion Inhibitor (B1-5) | mass % | — | — | — | — | — |
| | Corrosion Inhibitor (B2-1) | mass % | — | — | 2 | — | — |
| | Corrosion Inhibitor (B2-2) | mass % | — | — | — | 2 | — |
| | Corrosion Inhibitor (B2-3) | mass % | — | — | — | — | 2 |
| | Total | mass % | 100 | 100 | 100 | 100 | 100 |
| Physical Data | 40° C. Kinematic Viscosity | $mm^2/s$ | 25.08 | 21.34 | — | 36.86 | — |
| | 100° C. Kinematic Viscosity | $mm^2/s$ | 5.662 | 5.170 | — | 7.213 | — |
| | Viscosity Index | — | 177 | 187 | — | 164 | — |
| Evaluation Item | Solubility (appearance) | — | transparent | transparent | insoluble | transparent | insoluble |
| | Low Evaporability (evaporation amount) | mass % | <0.1 | <0.1 | — | >0.1 | — |
| | Metal Corrosion Resistance | — | B | B | — | A | — |

As known from Table 2, the lubricant compositions of Examples 1 to 6 satisfying all the constitution of the present invention are excellent in metal corrosion resistance, solubility and low evaporability. In addition, the lubricant compositions of Examples 1 to 6 all contain the corrosion inhibitor (B) and the ionic liquid (A) having a 5% mass reduction temperature of 270° C. or higher, and are therefore excellent in stability in high-temperature environments.

On the other hand, as shown in Table 3, the lubricant compositions of Comparative Examples 1 and 2 did not contain the corrosion inhibitor (B) and therefore the metal corrosion resistance thereof was insufficient. In the lubricant compositions of Comparative Examples 3 and 5, the corrosion inhibitor did not dissolve in the ionic liquid, and therefore the kinematic viscosity of the lubricant compositions could not be measured. Further, the evaporation amount from the lubricant composition of Comparative Example 4 was more than 0.1% by mass, and the low evaporability of the lubricant composition was insufficient. In addition, the 5% mass reduction temperature of the corrosion inhibitor contained in Comparative Examples 4 and 5 was lower than 270° C., and therefore there is a possibility that the lubricant compositions of these Comparative Examples could not be used in space environment of high-temperature environments.

The invention claimed is:

1. A compound of formula (B1):

(B1)

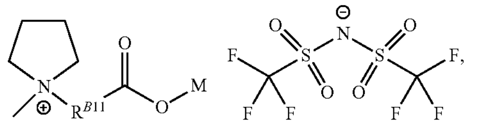

wherein

M is an alkali metal, and $R^{B11}$ is an alkylene group comprising 3 to 19 carbon atoms.

2. A corrosion inhibitor (B), comprising:

the compound of claim 1.

3. A lubricant composition, comprising:

an ionic liquid (A); and the corrosion inhibitor (B) of claim 2.

4. The lubricant composition of claim 3, wherein the ionic liquid (A) comprises a cation of formula (A1):

(A1)

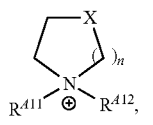

wherein n is 1 or 2,

X is a methylene group or oxygen, $R^{A11}$ and $R^{A12}$ are each independently an alkyl group having 1 to 12 carbon atoms, optionally comprising an ether group, an ester group, a nitrile group, and/or a silyl group.

5. The lubricant composition of claim 3, wherein the ionic liquid (A) comprises a compound of formula (A2):

(A2)

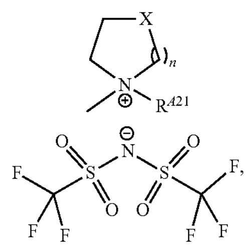

wherein n is 1 or 2,

X is a methylene group or oxygen, and $R^{A21}$ is an alkyl group comprising 2 to 12 carbon atoms.

6. The lubricant composition of claim 3, comprising the compound of formula (B1) in a range of from 0.1 to 10% by mass, based on a total lubricant composition mass.

7. The lubricant composition of claim 3, wherein a (B1/A) mass ratio of the content of the compound of formula (B1) to the content of the ionic liquid (A), is in a range of from 0.0005 to 0.15.

8. A lubricant composition, comprising:

an ionic liquid (A) comprising a cation of formula (A1):

(A1)

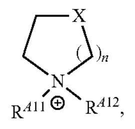

n being 1 or 2, X being a methylene group or oxygen, and $R^{A11}$ and $R^{A12}$ each independently being an alkyl group comprising 1 to 12 carbon atoms, optionally comprising an ether group, an ester group, a nitrile group, and/or a silyl group; and a corrosion inhibitor of formula (B1):

(B1)

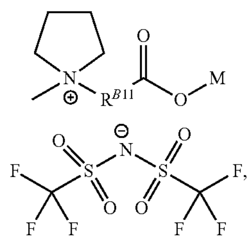

M being an alkali metal, and $R^{B11}$ being an alkylene group comprising 1 to 19 carbon atoms.

9. A lubricant composition, comprising:

a corrosion inhibitor of formula (B1):

(B1)

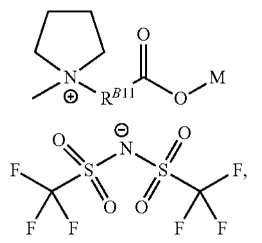

M being an alkali metal, and $R^{B11}$ being an alkylene group comprising 1 to 19 carbon atoms; and an ionic liquid (A) comprising a compound of formula (A2):

(A2)

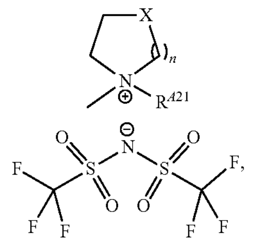

n being 1 or 2, X being a methylene group or oxygen, $R^{A21}$ being an alkyl group comprising 2 to 12 carbon atoms; and/or a compound of formula (A3):

(A3)

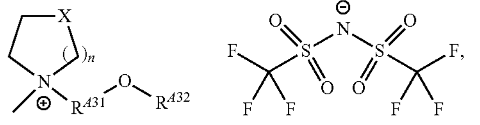

n being 1 or 2, X being a methylene group or oxygen, $R^{A31}$ being an alkylene group comprising 1 to 5 carbon atoms, $R^{A32}$ being a hydrogen atom or an alkyl group comprising 1 to 3 carbon atoms.

10. The lubricant composition of claim 9, wherein the ionic liquid (A) comprises the compound of formula (A2).

11. The lubricant composition of claim 9, wherein the ionic liquid (A) comprises the compound of formula (A3).

12. The lubricant composition of claim 9, wherein the ionic liquid (A) comprises the compound of formula (A2) and the compound of formula (A3).

13. The compound of claim 1, wherein the alkylene group of $R^{B11}$ in formula (B1) comprises 3 to 17 carbon atoms.

14. The compound of claim 1, wherein the alkylene group of $R^{B11}$ in formula (B1) comprises 5 to 19 carbon atoms.

15. The compound of claim 1, wherein the alkylene group of $R^{B11}$ in formula (B1) comprises 7 to 19 carbon atoms.

16. The lubricant composition of claim 3, wherein the ionic liquid (A) comprises a compound of formula (A3):

(A3)

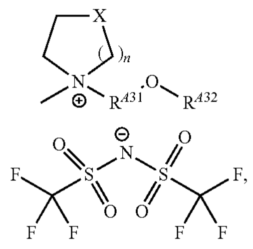

wherein n is 1 or 2,

X is a methylene group or oxygen, $R^{A31}$ is an alkylene group comprising 1 to 5 carbon atoms, and $R^{A32}$ is a hydrogen atom or an alkyl group comprising 1 to 3 carbon atoms.

17. The lubricant composition of claim 3, wherein the ionic liquid (A) comprises:

a compound of formula (A2):

(A2)

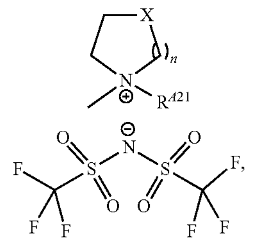

n being 1 or 2, X being a methylene group or oxygen, $R^{A21}$ being an alkyl group comprising 2 to 12 carbon atoms; and a compound of formula (A3):

(A3)

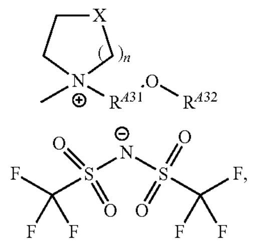

n being 1 or 2, X being a methylene group or oxygen, $R^{A31}$ being an alkylene group comprising 1 to 5 carbon atoms, $R^{A32}$ being a hydrogen atom or an alkyl group comprising 1 to 3 carbon atoms.

18. The lubricant composition of claim 4, wherein, in formula (A1), n is 1.

19. The lubricant composition of claim 4, wherein, in formula (A1), n is 2.

20. The lubricant composition of claim 4, wherein, in formula (A1), X is the methylene group.

* * * * *